United States Patent [19]

McPhail et al.

[11] Patent Number: 4,977,268

[45] Date of Patent: Dec. 11, 1990

[54] BORON DIPEPTIDE COMPOUNDS

[75] Inventors: Andrew T. McPhail, Durham; Bernard F. Spielvogel, Raleigh; Iris H. Hall, Chapel Hill, all of N.C.

[73] Assignee: Duke University, Durham, N.C.

[21] Appl. No.: 179,555

[22] Filed: Apr. 8, 1988

[51] Int. Cl.$^5$ .................... C07C 103/52; C07C 5/02
[52] U.S. Cl. ................................ 548/110; 556/7
[58] Field of Search ..................... 556/7; 548/110

[56] References Cited

U.S. PATENT DOCUMENTS

| | | | |
|---|---|---|---|
| 4,209,510 | 6/1980 | Spielvogel et al. | 424/144 |
| 4,312,989 | 1/1982 | Spielvogel et al. | 546/13 |
| 4,368,194 | 1/1983 | Spielvogel et al. | 424/185 |
| 4,499,082 | 2/1985 | Shenui et al. | 514/2 |
| 4,587,359 | 5/1986 | Spielvogel et al. | 546/8 |

FOREIGN PATENT DOCUMENTS 0190597 8/1986 European Pat. Off. ............. 514/18

OTHER PUBLICATIONS

Spielvogel, "Synthesis and Biological Activity of Boron Analogues of the a-Amino Acids and Related Compounds", *Boron Chemistry*, Pergamon Press Oxford and New York, 1980, pp. 119-129.

Klausner and Bodansky, "Coupling Reagents in Peptide Synthesis", *Synthesis* Sep., 1972, pp. 453-463.

Hall, Das, Harchelroad, Wisian-Neilson, McPhail and Spielvogel, "Antihyperlipidemic Activity of Amine Cyanoboranes, and Related Compounds", *Journal of Pharmaceutical Sciences*, vol. 70, No. 3, Mar. 1981, 339-341.

"The Organic Chemistry of Peptides", H. D. Law, pp. 91-93.

Jakubke and Jeschkeit, "Amino Acids, Peptides and Proteins", *Akademic-Verlag*, Berlin, 1977, pp. 108-111.

Scheller, Martin, Spielvogel and McPhail, "Basicity and Metal Ion Binding Capability of Amine-Carboxyboranes, $R_3N \cdot BH_2COOH$, Boron Analogs of Glycine and N-Methylated Glycines", *Inorganica Chimica Acta*, 57, 1982, pp. 227-228.

Spielvogel, Das, McPhail, Onan and Hall, "Boron Analogues of the a-Amino Acids, Synthesis, X-ray Crystal Structure, and Biological Activity of Ammonia-Carboxyborane, the Boron Analogue of Glycine", *Journal of the American Chemical Society*, 1980, pp. 6343-6343.

Silvey, Gary Lee, "Synthesis and Single-Crystal X-Ray Analysis of Dipeptides Involving Boron Analogs of a-Amino Acids", pp. iii-iv.

Das and Mukherjee, "Amine-Carboxyboranes, the Boron Analogues of a-Amino Acids: Synthesis, Acidity Constants, and Amide-Bond Formation", Jadavpur Chemistry Research, Calcutta, India, 1987, p. 368.

*Primary Examiner*—David B. Springer
*Attorney, Agent, or Firm*—Richard E. Jenkins

[57] ABSTRACT

Novel boron dipeptide analogs and their corresponding amide derivatives which exhibit significant antihyperlipidemic and antineoplastic activities. Methods for preparing the boron containing compounds are disclosed as well as methods for utilizing the compounds to induce antihyperlipidemic and antineoplastic activity.

8 Claims, No Drawings

BORON DIPEPTIDE COMPOUNDS

TECHNICAL FIELD

This invention relates to boron-containing compounds. More specifically, the present invention relates to novel boron dipeptide analogs which exhibit improved antineoplastic and antihyperlipidemic activity. The present invention also relates to methods for preparing and utilizing the novel boron dipeptide analogs.

BACKGROUND ART

The search for new and effective antineoplastic and antihyperlipidemic agents is continually expanding into new areas of technology. Recent advancements have been made in the field of boron chemistry and more specifically, amine borane compounds such as $Me_3N.BH_2COOH$ and $R_1R_2NH.BH_2C(O)NHR_3$ have been shown to exhibit antitumor and antihyperlipidemic activities. See U.S. Pat. No. 4,587,359. However, these compounds contain a relatively large amount of boron which is potentially toxic and therefore hazardous to the health of an animal or human undergoing treatment. These compounds are also poor carriers and have problems with solubility. A compound which contains a relatively small amount of boron but still exhibits significant antitumor and antihyperlipidemic activity has yet to be developed.

It is well known in traditional non-boron organic chemistry to synthesize a peptide bond by the reaction of various amino acids in the presence of a coupling reagent. One of the most widely used coupling reagents in organic peptide synthesis is N,N'-dicyclohexylcarbodiimide (DDC). [H. D. Law, "The Organic Chemistry of Peptides", Wiley-Interscience, New York, N.Y., p. 90 (1970). H. D. Jakubke and H. Jeschkeit, "Akademie-Verlag", Berlin, p. 108 (1977)]. In the organic coupling reaction, the nitrogen atom of one amino acid attacks the carbonyl carbon of the carboxylic acid portion of the other amino acid in order to form a peptide bond.

Peptide bond formation with a boron-containing amino acid such as $Me_3N.BH_2CO_2H$ would not be expected because of the formal negative charge on the boron atom next to the carbonyl group. The replacement of carbon in an amino acid by boron has a dramatic effect on the relative $K_a$ for the boron amino acids versus the normal amino acids since boron is much less electronegative than carbon. The $pK_a$ for $Me_3N.BH_2CO_2H$ is about six log units more basic than the carboxylic acid group in $Me_3N^+CH_2CO_2H$. [K. H. Scheller, R. B. Martin, B. F. Spielvogel and A. T. McPhail, "Inorganic Chemica Acta" 57, 227 (1982)]. The resulting formal negative charge on the boron atom renders the carbonyl carbon in $Me_3N.BH_2CO_2H$ much less susceptible to nucleophilic attack by an incoming amine group of an amino acid. Therefore, it would not be expected that a boron dipeptide analog could be prepared utilizing traditional organic coupling reagents and amino acid techniques. A process for producing a boron dipeptide analog has heretofore not been developed.

DISCLOSURE OF THE INVENTION

One aspect of the present invention relates to novel boron compounds which contain a relatively small amount of boron but surprisingly exhibit substantial antitumor and antihyperlipidemic activity. The boron compounds of the present invention are also efficient carriers and exhibit favorable solubility characteristics.

The boron dipeptide analogs of the present invention correspond to the general formula:

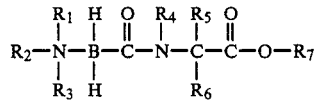

wherein $R_1$, $R_2$, $R_3$, $R_4$, $R_5$ and $R_7$ can be the same or different and are H or $C_1$-$C_{18}$ alkyl and wherein $R_6$ is H or $C_1$-$C_{18}$ alkyl, $C_1$-$C_{18}$ thioalkyl, $C_1$-$C_{18}$ alkanol, $C_1$-$C_{18}$ alkylphenol, $C_1$-$C_{18}$ arylalkyl, $C_1$-$C_{18}$ alkylamine, $C_1$-$C_{18}$ alkylamide, $C_1$-$C_{18}$ alkylcarboxylic acid, $C_1$-$C_{18}$ alkylguanidino, $C_1$-$C_{18}$ alkylindole or $C_1$-$C_{18}$ alkylimidazole and further wherein $R_4$ can be bonded to $R_6$ so as to form a $C_4$-$C_{10}$ heterocyclic ring system.

The boron dipeptide amide analogs of the present invention correspond to the general formula:

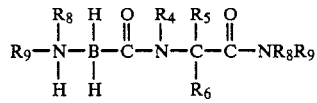

wherein $R_4$, $R_5$, and $R_6$ are as defined hereinbefore and $R_8$ and $R_9$ can be the same or different and are H or $C_1$-$C_{18}$ alkyl.

Another aspect of the present invention relates to processes for preparing the novel boron-containing compounds disclosed herein. It has surprisingly been found that a boron dipeptide analog can be produced using the organic coupling reagent dicyclohexylcarbodiimide. Accordingly, one process of the present invention comprises contacting an amino acid alkyl ester with a trialkylamine-carboxyborane in the presence of dicyclohexylcarbodiimide under reaction conditions sufficient to form a boron dipeptide analog. Another process of the present invention comprises reacting the resulting boron dipeptide analog with an appropriate amine to form the corresponding boron dipeptide amide analog.

It is therefore an object of the present invention to provide a compound which can be safely and effectively used as an antineoplastic and antihyperlipidemic agent.

It is another object of the present invention to provide a boron-containing compound that contains a relatively small amount of boron yet exhibits an effective amount of antineoplastic and antihyperlipidemic activity.

It is another object of the present invention to provide a boron-containing compound which is an effective carrier and exhibits desirable solubility characteristics.

It is still another object of the present invention to provide a process for preparing the novel boron-containing compounds of the present invention.

It is yet another object of the present invention to provide a method for inducing antineoplastic and antihyperlipidemic activity in an animal in need of such treatment.

BEST MODE FOR CARRYING OUT THE INVENTION

The novel boron-containing compounds of the present invention contain a peptide bond formed by the reaction of an amino acid alkyl ester with a trialkylamine-carboxyborane. The boron dipeptide analogs of the present invention correspond to the following general formula:

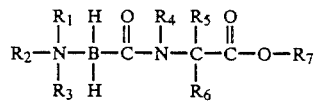

wherein $R_1$, $R_2$, $R_3$, $R_4$, $R_5$ and $R_7$ can be the same or different and are H or $C_1$-$C_{18}$ alkyl and wherein $R_6$ is H or $C_1$-$C_{18}$ alkyl, $C_1$-$C_{18}$ thioalkyl, $C_1$-$C_{18}$ alkanol, $C_1$-$C_{18}$ alkylphenol, $C_1$-$C_{18}$ arylalkyl, $C_1$-$C_{18}$ alkylamine, $C_1$-$C_{18}$ alkylamide, $C_1$-$C_{18}$ alkylcarboxylic acid, $C_1$-$C_{18}$ alkylguanidino, $C_1$-$C_{18}$ alkylindole or $C_1$-$C_{18}$ alkylimidazole and further wherein $R_4$ can be bonded to $R_6$ so as to form a $C_4$-$C_{10}$ heterocyclic ring system.

$C_m$-$C_n$ herein refers to a branched, straight chain or cyclic carbon chain ranging from m to n carbon atoms. Thioalkyl refers to an alkyl chain having a sulfur atom attached at any position along the carbon chain. Alkanol, alkylphenol and arylalkyl herein refer to alkyl chains having an OH group, a phenolic group and an aryl group, respectively, attached at any position along the carbon chain. Alkylguanidino, alkylindole and alkylimidazole herein refer to alkyl chains having a guanidino group, an indole group and an imidazole group, respectively, attached at any position along the carbon chain.

Preferably $R_1$, $R_2$, and $R_3$ are selected so as to not sterically hinder the formation of the boron-nitrogen bond and are preferably H or $C_1$-$C_5$ alkyl. $R_4$, $R_5$ and $R_7$ are preferably H or $C_1$-$C_8$ alkyl; $R_6$ is preferably H or $C_1$-$C_8$ alkyl, $C_1$-$C_8$ thioalkyl, $C_1$-$C_8$ alkanol, $C_1$-$C_8$ alkylphenol, $C_1$-$C_8$ arylalkyl, $C_1$-$C_8$ alkylamine, $C_1$-$C_8$ alkylamide, $C_1$-$C_8$ alkylcarboxylic acid, $C_1$-$C_8$ alkylguanidino, $C_1$-$C_8$ alkylindole or $C_1$-$C_8$ alkylimi-dazole; and $R_4$ is preferably bonded to $R_6$ so as to form a $C_4$-$C_7$ heterocyclic ring system. $R_1$, $R_2$ and $R_3$ are most preferably all $CH_3$; $R_4$ and $R_5$ are most preferably H and $R_7$ is most preferably $CH_3$. $R_6$ is most preferably H, $CH_3$, $CH_2CH_2SCH_3$,

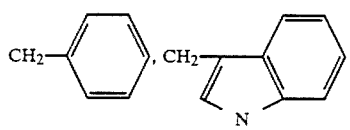

or $CH_2OH$.

The boron dipeptides are named according to the amino acid from which they are derived. The most preferred boron dipeptides of the present invention include N-[(Trimethylamine-boryl)carbonyl]-L-alanine methyl ester, N-[(Trimethylamine-boryl)carbonyl]-L-serine methyl ester, N-[(Trimethylamine-boryl) carbonyl]-L-proline methyl ester, N-[(Trimethylamine-boryl)carbonyl]-L-phenylalanine methyl ester, N-[(Trimethylamine-boryl) carbonyl]-L-tryptophan methyl ester, N-[(Trimethylamineboryl)carbonyl]glycine methyl ester and N-[(Trimethylamine-boryl)carbonyl]-L-methionine methyl ester.

The amide derivatives of the above compounds are also contemplated by the present invention and are formed by reacting a boron dipeptide analog with an appropriate amine. The amide derivative compounds are herein referred to as boron dipeptide amide analogs and correspond to the following formula:

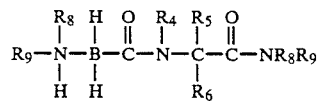

wherein $R_4$, $R_5$, and $R_6$ are as defined hereinbefore and $R_8$ and $R_9$ can be the same or different and are H or $C_1$-$C_{18}$ alkyl. $R_8$ and $R_9$ are preferably selected so as to not sterically hinder the formation of the boron-nitrogen bond and are preferably H or $C_1$-$C_5$ alkyl. $R_8$ and $R_9$ are both most preferably H. The most preferred boron dipeptide amide analogs of the present invention include N-[(Ammonia-boryl)carbonyl] alanine amide, N-[(Ammoniaboryl)carbonyl]serine amide, N-[(Ammonia-boryl) carbonyl] proline amide, N-[(Ammonia-boryl)carbonyl]phenylalanine amide, N-[(Ammonia-boryl)carbonyl]tryptophan amide, N-[(Ammonia-boryl)carbonyl] glycine amide and N-[(Ammonia-boryl)carbonyl] methionine amide.

Due to their peptide nature, the boron-containing compounds of the present invention contain a relatively smaller amount of boron per molecule than prior art boron compounds. It has surprisingly been discovered that the reduced amount of boron per molecule does not result in a corresponding reduction in pharmaceutical activity. The lower amount of boron in the present compounds minimizes the possibility of boron toxicity problems in an animal or human being treated. The boron compounds also have increased solubility and are effective carriers.

One process of the present invention involves the formation of a peptide bond by reacting an amino acid alkyl ester with a trialkylamine-carboxyborane in the presence of dicyclohexylcarbodiimide. The amino acid alkyl esters of the present invention are derived from the well known amino acids and correspond to the following general formula:

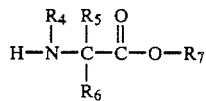

wherein $R_4$, $R_5$, $R_6$ and $R_7$ are as defined hereinbefore. The most preferred amino acid alkyl esters of the present invention include L-alanine methyl ester, L-serine methyl ester, L-proline methyl ester, L-phenylalanine methyl ester, L-tryptophan methyl ester, glycine methyl ester and L-methionine methyl ester.

The trialkylamine-carboxyboranes of the present invention correspond to the formula:

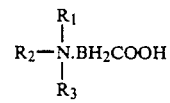

wherein $R_1$, $R_2$ and $R_3$ are as defined hereinbefore. Preferred trialkylamine-carboxyborane compounds of the present invention include trimethylamine-carboxyborane and triethylamine-carboxyborane with trimethylaminecarboxyborane being the most preferred. The trialkylamine-carboxyboranes of the present invention can be prepared using techniques disclosed in U.S. Pat.

No. 4,312,989 and in B. F. Spielvogel et al., J. Am. Chem. Soc., 93, p. 5702 (1976).

The first step of the process involves contacting the hydrohalide salt of an amino acid alkyl ester with a trialkylamine. The hydrohalide salt of the amino acid alkyl ester is preferably utilized in a suitable solvent such as methylene chloride or tetrahydrofuran. The preferred salt is the hydrochloride salt while methylene chloride is the preferred solvent. The alkyl group of the trialkylamine can be $C_1$–$C_{18}$ alkyl, is preferably $C_1$–$C_5$ alkyl and is most preferably ethyl. The trialkylamine is added to the hydrohalide salt of the amino acid and the mixture is stirred for at least 20 minutes. Since the purpose of the trialkylamine is to free the amino acid alkyl ester of the hydrohalide, this first step can be omitted if the amino acid alkyl ester is not utilized in the form of a salt.

The next step involves adding the trialkylaminecarboxyborane and the N,N'-dicyclohexylcarbodiimide (DCC) to the reaction mixture. The trialkylamine-carboxyborane and the DCC are preferably dissolved in a suitable solvent such as methylene chloride or tetrahydrofuran. The most preferred solvent is methylene chloride.

The resulting mixture is maintained for 72 hours after which the desired product is isolated using known distillation, precipitation, filtration and crystallization techniques.

It has also been discovered that the boron dipeptide analog resulting from the above process can be converted into the corresponding boron dipeptide amide analog by reaction with an amine corresponding to the following formula:

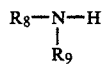

wherein $R_8$ and $R_9$ are as defined hereinbefore. $R_8$ and $R_9$ can essentially be any combination of alkyl groups so long as the groups are not so bulky as to sterically hinder the nitrogen from reacting with the boron atom of the boron dipeptide. Preferable amines include dimethylamine, methylamine, ethylamine, propylamine, butylamine and ammonia with ammonia being the most preferred.

The amide formation process is carried out by reacting an amine with the boron dipeptide analog at a temperature below $-70°$ and allowing the reaction mixture to reach room temperature. The reaction mixture is maintained at room temperature for at least three weeks and the resulting boron dipeptide amide analog is removed by standard techniques.

It should be noted that during the reaction the amine not only attacks the carbonyl carbon of the organic amino acid ester portion of the boron dipeptide analog but also may replace the amine group associated with the boron atom. For example, ammonia will definitely replace an alkyl amine group associated with the boron atom and whether or not another amine group will replace other groups depends on the relative affinities of the amines for the boron atom. The resulting amide derivatives exhibit antineoplastic and antihyperlipidemic activities similar to the parent boron dipeptide analogs.

The compounds of the present invention can be administered to an animal in therapeutically effective amounts utilizing well known administration techniques and carriers. Therapeutically effective amount herein refers to an amount sufficient to bring about a desired level of pharmaceutical activity. Due to the unknown toxic effect of boron compounds, actual human tests have not been conducted. Nevertheless, the present invention fully contemplates the use of the present boron compounds on human subjects in order to treat cancer and control serum lipid levels and animal as used herein is intended to include humans. The results of specific tests for antihyperlipidemic activity and antineoplastic activity are shown in Tables 1 and 2.

SPECIFIC EMBODIMENTS

The following examples are included for the purpose of illustration only and are not to be construed to limit the scope of the invention or claims. Unless otherwise indicated, all parts and percentages are by weight.

PREPARATION OF BORON DIPEPTIDE ANALOGS

EXAMPLE 1

N-[(Trimethylamine-boryl)carbonyl]-L-alanine methyl ester (1). To a solution of L-alanine methyl ester hydrochloride (5.97 g, 42.8 mmol) in $CH_2Cl_2$ (100 ml) was added $Et_3N$ (4.33 g, 42.8 mmol), and the mixture was stirred for 20 minutes at room temperature. A solution of $Me_3N.BH_2COOH$ (5.00 g, 42.8 mmol) in $CH_2Cl_2$ (50 ml) was then added to the reaction mixture, followed by N,N'-dicyclohexylcarbodiimide (DCC) (9.27 g, 49.1 mmol) in $CH_2Cl_2$ (50 ml). After 72 hours, the N,N'-dicyclohexylurea (DCU) precipitate which formed was filtered off, and the solvent was removed under reduced pressure. The solid residue was then washed with diethyl ether ($3\times300$ ml), and the combined washes were filtered prior to removal of the ether under reduced pressure. This procedure was repeated with water ($3\times300$ ml) as solvent, following which, evaporation of the water from the combined washes was aided by passage of a dry air stream over the solution. Further purification of the resulting yellow oil was performed by flash chromatography using ethyl acetate/acetone (95:5) as the mobile phase. After the peptide-containing fractions were combined and the solvent removed in vacuo, the peptide oil was distilled under vacuum at 50° C. Final purification of the distilled oil was performed by flash chromatography on a column packed with petroleum ether and eluted with ethyl acetate/n-butyl alcohol (95:5). The peptide-containing fractions were combined, and the solvent was removed by the passage of a dry air stream over the solution to give the desired crystalline dipeptide. (Due to the hygroscopic nature of (1), a clear oil may result, which may be crystallized by storage under high-vacuum for several weeks.) Yield: 0.452 g (5.23%).

EXAMPLE 2

N-[(Trimethylamine-boryl)carbonyl]-L-serine methyl ester (2). To a solution of L-serine methyl ester hydrochloride (6.65 g, 42.8 mmol) in $CH_2Cl_2$ (100 ml) was added $Et_3N$ (4.33 g, 42.8 mmol), and the mixture was stirred for 20 minutes at room temperature. A solution of $Me_3N.BH_2COOH$ (5.00 g, 42.8 mmol) in $CH_2Cl_2$ (50 ml) was then added to the reaction mixture, followed by DCC (9.266 g, 49.1 mmol) in $CH_2Cl_2$ (50 ml). After 72 hours, the DCU precipitate which formed was filtered off, and the solvent was removed under reduced pressure. The solid residue was then washed with diethyl ether (3×300 ml), and the combined washes were filtered prior to removal of the ether under reduced pressure. This procedure was repeated with water (3×300 ml) as solvent, following which, evaporation of the water from the combined washes was aided by passage of a dry air stream over the solution. Further purification of the oily residue was performed by flash chromatography using one liter of ethyl acetate/acetone (95:5) followed by ethyl acetate/acetone (1:1) as the mobile phase. The peptide-containing fractions were combined and the solvent removed in vacuo. Final purification was performed by flash chromatography using ethyl acetate/acetone (6:4) plus $Et_3N$ (2.5 ml per liter) as the mobile phase. After removal of the solvent (in vacuo) from the peptide-containing fractions, the dipeptide was recrystallized from acetone/ethyl ether/petroleum ether (1:4:5) to yield 0.673 g (7.21%).

EXAMPLE 3

N-[(Trimethylamine-boryl)carbonyl]-L-proline methyl ester (3). To a solution of L-proline methyl ester hydrochloride (6.53 g, 42.8 mmol) in $CH_2Cl_2$ (100 ml) was added $Et_3N$ (4.33 g, 42.8 mmol), and the mixture was stirred for 20 minutes at room temperature. A solution of $Me_3N.BH_2COOH$ (5.00 g, 42.8 mmol) in $CH_2Cl_2$ (50 ml) was then added to the reaction mixture, followed by DCC (9.266 g, 49.1 mmol) in $CH_2Cl_2$ (50 ml). After 72 hours, the DCU precipitate which formed was filtered off, and the solution was washed with 1N HCl (20 ml), 1N $K_2CO_3$ (20 ml), and water (20 ml), respectively. After drying over $MgSO_4$ and filtering, the solvent was removed under reduced pressure. The solid residue was then washed with diethyl ether (3×300 ml), and the combined washes were filtered prior to removal of the ether under reduced pressure. This procedure was repeated with water (3×300 ml) as solvent, following which, evaporation of the water from the combined washes was aided by passage of a dry air stream over the solution. The residue was placed in a sublimator and any remaining unreacted $Me_3N.BH_2COOH$ was removed by sublimation under vacuum at 40° C. for three hours. The crude product was dissolved in $CH_2Cl_2$ (20 ml), and pentane was added until the solution became cloudy. After cooling to −30° C. overnight, the solvent was decanted, leaving (3) as a white precipitate. Final purification of the dipeptide was accomplished by repeating the recrystallization technique above, resulting in long needles of (3), for a yield of 0.240 g (2.46%).

EXAMPLE 4

N-[(Trimethylamine-boryl)carbonyl]-L-phenylalanine methyl ester (4). To a solution of L-phenylalanine methyl ester hydrochloride (9.22 g, 42.8 mmol) in $CH_2Cl_2$ (100 ml) was added $Et_3N$ (4.33 g, 42.8 mmol), and the mixture was stirred for 20 minutes at room temperature. A solution of $Me_3N.BH_2COOH$ (5.00 g, 42.8 mmol) in $CH_2Cl_2$ (50 ml) was then added to the reaction mixture, followed by DCC (9.266 g, 49.1 mmol) in $CH_2Cl_2$ (50 ml). After 72 hours, the DCU precipitate which formed was filtered off, and the solvent was removed under reduced pressure. The solid residue was then washed with diethyl ether (3×300 ml), and the combined washes were filtered prior to removal of the ether under reduced pressure. This procedure was repeated with water (3×300 ml) as solvent, following which, evaporation of the water from the combined washes was aided by passage of a dry air stream over the solution. The residue was dissolved in $CHCl_3$ (20 ml), and pentane was added until the solution became cloudy. The resulting solution was stored at −30° C. overnight. The next day the $CHCl_3$ soluble material was decanted and the solvent removed under reduced pressure. Final purification of the residue was performed by flash chromatography using ethyl acetate/acetone (95:5) as the mobile phase. The peptide-containing fractions were combined and the solvent removed in vacuo. Recrystallization of the purified dipeptide from ethyl ether/petroleum ether (3:1) under nitrogen yielded 1.15 g (9.69%).

EXAMPLE 5

N-[(Trimethylamine-boryl)carbonyl]-L-tryptophan methyl ester (5). To a solution of L-tryptophan methyl ester hydrochloride (21.8 g, 85.5 mmol) in $CH_2Cl_2$ (200 ml) was added $Et_3N$ (8.70 g, 85.5 mmol), and the mixture was stirred for 20 minutes at room temperature. A solution of $Me_3N.BH_2COOH$ (10.00 g, 85.5 mmol) in $CH_2Cl_2$ (50 ml) was then added to the reaction mixture, followed by DCC (17.7 g, 85.5 mmol) in $CH_2Cl_2$ (50 ml). After 72 hours, the DCU precipitate which formed was filtered off, and the solvent was removed under reduced pressure. The solid residue was then washed with acetone (3×100 ml), and the combined washes were filtered prior to removal of the acetone under reduced pressure. The residue was partially purified by flash chromatography using ethyl acetate/acetone (8:2) plus $Et_3N$ (2.5 ml per liter) as the mobile phase. The peptide-containing fractions were combined and the solvent removed under reduced pressure. Final purification of the dipeptide was performed by flash chromatography using ethyl acetate/n-butyl alcohol (8:2) plus $Et_3N$ (2.5 ml per liter) as the elutant. After combining the peptide-containing fractions and removal of the solvent in vacuo, the dipeptide was dissolved in $CH_2Cl_2$ (5 ml), and petroleum ether was added until the solution was cloudy. After storage overnight at −30° C., crystals of (5) formed for a yield of 0.060 g (0.221%).

EXAMPLE 6

N-[(Trimethylamine-boryl)carbonyl]glycine methyl ester (6). To a solution of glycine methyl ester hydrochloride (5.37 g, 42.8 mmol) in $CH_2Cl_2$ (100 ml) was added $Et_3N$ (4.33 g, 42.8 mmol), and the mixture was stirred for 20 minutes at room temperature. A solution of $Me_3N.BH_2COOH$ (5.00 g, 42.8 mmol) in $CH_2Cl_2$ (50 ml) was then added to the reaction mixture, followed by DCC (9.266 g, 49.1 mmol) in $CH_2Cl_2$ (50 ml). After 72 hours, the DCU precipitate which formed was filtered off, and the solvent was removed under reduced pressure. The solid residue was then washed with diethyl ether (3×300 ml), and the combined washes were filtered prior to removal of the ether under reduced pressure. This procedure was repeated with water (3×300 ml) as solvent, following which, evaporation of the water from the combined washes was aided by passage of a dry air stream over the solution. Final purification was accomplished by use of one of two procedures: (1) Recrystallization of the crude product from $CH_2Cl_2$/heptane (2:1), then washing the resulting crystals with a small amount of acetone to remove any yellow coloration, followed by sublimation to remove any remaining unreacted $Me_3N.BH_2COOH$; or (2) flash chromatography using ethylacetate/acetone (9:1) as the mobile phase. After combining the peptide-containing fractions and removal of the solvent in vacuo, the purified product was recrystallized from acetone/heptane (1:1) to yield 2.01 g (25.1%) of (6).

EXAMPLE 7

N-[(Trimethylamine-boryl)carbonyl]-L-methionine methyl ester (7). To a solution of L-methionine methyl ester hydrochloride (8.54 g, 42.8 mmol) in $CH_2Cl_2$ (100 ml) was added $Et_3N$ (4.33 g, 42.8 mmol), and the mixture was stirred for 20 minutes at room temperature. A solution of $Me_3N.BH_2COOH$ (5.00 g, 42.8 mmol) in $CH_2Cl_2$ (50 ml) was then added to the reaction mixture, followed by DCC (9.266 g, 49.1 mmol) in $CH_2Cl_2$ (50 ml). After 72 hours, the DCU precipitate which formed was filtered off, and the solvent was removed under reduced pressure. The solid residue was then washed with diethyl ether (3×300 ml), and the combined washes were filtered prior to removal of the ether under reduced pressure. This procedure was repeated with water (3×300 ml) as solvent, following which, evaporation of the water from the combined washes was aided by passage of a dry air stream over the solution. The residue was dissolved in $CHCl_3$ (20 ml), and pentane was added until the solution was cloudy. After storage overnight at −40° C., the $CHCl_3$/pentane soluble fraction was decanted off and the solvent removed under reduced pressure. Any remaining unreacted $Me_3B.BH_2COOH$ was removed by sublimation under vacuum at 40° C. for three hours. Final purification of the dipeptide was performed by flash chromatography using ethyl acetate/acetone (95:5) as the mobile phase. The peptide-containing fractions were combined and the solvent removed in vacuo to yield 1.35 g (12.0%) of (7).

EXAMPLE 8

N-[(ammonia-boryl) carbonyl]glycine amide (8). To N-[(trimethylamine-boryl)carbonyl]glycine methyl ester (6) (0.222 g, 1.18 mmol) in a 250 ml glass pressure reaction vessel cooled to −78° C. was added liquid ammonia (40 ml). The vessel was sealed and allowed to warm to room temperature where it was maintained for three weeks. The pressure vessel was then cooled to −78° C., opened to the atmosphere, and placed in a hood to allow excess ammonia to evaporate. The crude product was washed with $CHCl_3$ (20 ml) to remove any unreacted starting material. Final purification involved drying the dipeptide in vacuo followed by recrystallization from water to yield 0.136 g (88.0%) of (8).

Antihyperlipidemic Screens

Compounds to be tested were suspended in 1% aqueous carboxymethylcellulose and administered to male $CF_1$ mice (25 g) intraperitoneally for 16d. On days 9 and 16, blood was obtained by tail vein bleeding, and the serum was separated by centrifugation for three minutes. The serum cholesterol levels were determined by a modification of the Liebermann-Burchard reaction [A. T. Ness, J. V. Pastewka, and A. C. Peacock, Clin. Chim. Acta, 10, 229 (1964)]. Serum triglyceride levels were determined with a commercial kit [Fisher, Hycel Triglyceride Test Kit] for a different group of animal bled on day 16. The results of the antihyperlipidemic screens are shown in Table 1.

TABLE 1

| Compound | Dose (mg/kg) | % Inhibition Serum Cholesterol Day 9 | % Inhibition Serum Cholesterol Day 16 | % Inhibition Serum Triglyceride Day 16 |
|---|---|---|---|---|
| I (a) | 20 | 31 | 52 | 30 |
|  | 8 | 21 | 42 | 59 |
| I (b) | 20 | 55 | 55 | 23 |
| I (c) | 20 | 25 | 48 | 33 |
| II | 8 | 21 | 42 | 53 |

I (a) N-[(trimethylamine-boryl)carbonyl] - glycine methyl ester
(b) N-[(trimethylamine-boryl)carbonyl] - L-methionine methyl ester
(c) N-[(trimethylamine-boryl)carbonyl] - L-phenylalanine methyl ester
II N-[(ammonia-boryl)carbonyl] - glycine amide

Antineoplastic Activity

Boron dipeptide analogs were investigated for potential antineoplastic activity in the Ehrlich ascites carcinoma in vivo screen in CF-1 mice and in cytotoxic assays involving the L-1210 lymphoid leukemia and P-388 lymphocytic leukemia cell lines. The activity compared favorably with standard commercially available agents as shown in Table 2. The $ED_{50}$ is the effective dosage required to kill 50 percent of the tumor cells in the leukemia cell culture.

TABLE 2

| R | R' | In Vivo % Inhibition of Ehrlich Ascites Carcinoma Growth | $ED_{50}$ (μg/ml) Cytotoxicity L-1210 Lymphoid Leukemia | $ED_{50}$ (μg/ml) Cytotoxicity P-388 Lymphocytic Leukemia |
|---|---|---|---|---|
| $H_3NBH_2C(O)NHC(R)HC(O)NH_2$ | | | | |
| 1. H | | 67 | 1.40 | 7.62 |
| 2. $CH_2OH$ | | 52 | 10.6 | 8.73 |
| 3. $CH_2CH_2SCH_3$ | | 75 | 4.17 | 8.57 |
| 4. $CH_2CH(CH_3)_2$ | | 46 | 3.60 | 11.61 |
| $H_3NBH_2C(O)NHC(R)HC(O)OCH_3$ | | | | |
| 5. R—$CH(CH_3)CH_2CH_3$ | | 77 | 14.7 | 9.8 |
| 6. R—$CH(CH_3)_2$ | | 87 | 3.44 | 3.98 |
| $(CH_3)_3NBH_2C(O)NHC(R)HC(O)OR'$ | | | | |
| 7. H | $CH_3$ | 89 | 7.00 | 12.11 |
| 8. $CH_2OH$ | $CH_3$ | 61 | 1.98 | 9.21 |
| 9. $CH_2CH_2SCH_3$ | $CH_3$ | 41 | 6.62 | 12.86 |
| 10. $CH(CH_3)_2$ | $CH_3$ | 60 | 12.62 | 15.19 |
| 11. $CH_2CH(CH_3)_2$ | $CH_3$ | 77 | 6.80 | 11.63 |
| 12. $CH(CH_3)CH_2CH_3$ | $CH_3$ | 74 | 10.51 | 10.82 |
| 13. $CH_2C_6H_5$ | $CH_3$ | 94 | 10.84 | 8.89 |
| 14. $CH_2C_6H_4OH$ | $CH_3$ | 81 | 4.03 | 9.36 |
| 15. $CH_3$ | tBu | 74 | 7.21 | 11.43 |
| 16. $CH_3$ | $CH_3$ | 83 | — | — |

TABLE 2-continued

| R | R' | In Vivo % Inhibition of Ehrlich Ascites Carcinoma Growth | ED$_{50}$ ($\mu$g/ml) Cytotoxicity | |
|---|---|---|---|---|
| | | | L-1210 Lymphoid Leukemia | P-388 Lymphocytic Leukemia |
| 17. (CH$_3$)$_3$NBH$_2$C(O)N(H)C(H)COOCH$_3$ with (CH$_2$)$_3$ bridge | | 96 | 4.09 | 11.47 |
| Standards: | | | | |
| Melphalan | | 99 | — | — |
| 6-Mercaptopurine | | 99.6 | 2.43 | 4.10 |
| 5-Fluorouracil | | — | 1.94 | 3.72 |
| Ara C | | — | 2.76 | 4.06 |

It will be understood that various details of the invention may be changed without departing from the scope of the invention. Furthermore, the foregoing description is for the purpose of illustration only, and not for the purpose of limitation—this invention being defined by the following claims.

What is claimed is:

1. A boron dipeptide analog corresponding to the general formula:

$$\begin{array}{c} R_1 \ \ H \ \ O \ \ R_4 \ R_5 \ O \\ | \ \ \ | \ \ \ || \ \ \ | \ \ | \ \ || \\ R_2-N-B-C-N-C-C-O-R_7 \\ | \ \ \ | \ \ \ \ \ \ \ \ | \\ R_3 \ \ H \ \ \ \ \ \ \ \ R_6 \end{array}$$

wherein R$_1$, R$_2$, R$_3$, R$_4$, R$_5$ and R$_7$ can be the same or different and are H or C$_1$-C$_{18}$ alkyl and wherein R$_6$ is H or C$_1$-C$_{18}$ alkyl, C$_1$-C$_{18}$ thioalkyl, C$_1$-C$_{18}$ alkanol, C$_1$-C$_{18}$ alkylphenol, C$_1$-C$_{18}$ arylalkyl, C$_1$-C$_{18}$ alkylamine, C$_1$-C$_{18}$ alkylamide, C$_1$-C$_{18}$ alkylcarboxylic acid, C$_1$-C$_{18}$ alkylguanidino, C$_1$-C$_{18}$ alkylindole or C$_1$-C$_{18}$ alkylimidazole and further wherein R$_4$ can be bonded to R$_6$ so as to form a pyrrolidino ring.

2. A boron dipeptide analog according to claim 1 wherein R$_1$, R$_2$, R$_3$ and R$_7$ are all CH$_3$ and R$_4$ and R$_5$ are both H.

3. A boron dipeptide analog according to claim 2 wherein R$_6$ is selected from the group consisting of H, CH$_3$, CH$_2$CH$_2$SCH$_3$,

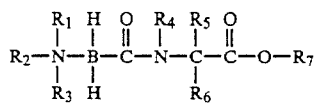

and CH$_2$OH.

4. A boron dipeptide analog according to claim 1 wherein R$_1$, R$_2$, R$_3$ and R$_7$ are all CH$_3$; R$_5$ is H; and wherein R$_4$ is bonded to R$_6$ to form a pyrrolidino ring.

5. A boron dipeptide amide analog corresponding to the formula:

$$\begin{array}{c} R_8 \ \ H \ \ O \ \ R_4 \ R_5 \ O \\ | \ \ \ | \ \ \ || \ \ \ | \ \ | \ \ || \\ R_9-N-B-C-N-C-C-NR_8R_9 \\ | \ \ \ | \ \ \ \ \ \ \ \ | \\ H \ \ H \ \ \ \ \ \ \ \ \ \ \ R_6 \end{array}$$

wherein R$_4$, R$_5$, R$_8$ and R$_9$ can be the same or different and are H or C$_1$-C$_{18}$ alkyl and wherein R$_6$ is H or C$_1$-C$_{18}$ alkyl, C$_1$-C$_{18}$ thioalkyl, C$_1$-C$_{18}$ alkanol, C$_1$-C$_{18}$ alkylphenol, C$_1$-C$_{18}$ arylalkyl, C$_1$-C$_{18}$ alkylamine, C$_1$-C$_{18}$ alkylamide, C$_1$-C$_{18}$ alkylcarboxylic acid, C$_1$-C$_{18}$ alkylguanidino, C$_1$-C$_{18}$ alkylindole or C$_1$-C$_{18}$ alkylimidazole and further wherein R$_4$ can be bonded to R$_6$ so as to form a pyrrolidino ring system.

6. A boron dipeptide amide analog according to claim 5 wherein R$_4$, R$_5$, R$_8$ and R$_9$ are all H.

7. A boron dipeptide amide analog according to claim 6 wherein R$_6$ is selected from the group consisting of H, CH$_3$, CH$_2$CH$_2$SCH$_3$,

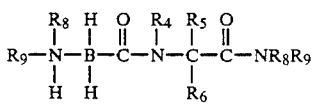

and CH$_2$OH.

8. A boron dipeptide amide analog according to claim 5 wherein R$_5$, R$_8$ and R$_9$ are all H and wherein R$_4$ is bonded to R$_6$ to form a pyrrolidino ring.

* * * * *